(12) United States Patent
Gvozdic

(10) Patent No.: US 8,840,989 B2
(45) Date of Patent: Sep. 23, 2014

(54) REINFORCED, LAMINATED, IMPREGNATED, AND COMPOSITE-LIKE MATERIALS AS CROSS-LINKED POLYVINYL ALCOHOL HYDROGEL STRUCTURES

(76) Inventor: Nedeljko Gvozdic, Gainesville, FL (US)

( * ) Notice: Subject to any disclaimer, the term of this patent is extended or adjusted under 35 U.S.C. 154(b) by 820 days.

(21) Appl. No.: 12/462,829

(22) Filed: Aug. 10, 2009

(65) Prior Publication Data

US 2009/0305024 A1    Dec. 10, 2009

Related U.S. Application Data

(60) Continuation-in-part of application No. 10/963,053, filed on Oct. 12, 2004, now abandoned, which is a division of application No. 10/020,785, filed on Oct. 29, 2001, now Pat. No. 6,855,743.

(51) Int. Cl.
| | |
|---|---|
| B32B 3/26 | (2006.01) |
| B29C 65/00 | (2006.01) |
| C08J 9/26 | (2006.01) |
| C08J 9/28 | (2006.01) |
| C08G 83/00 | (2006.01) |
| C08J 5/04 | (2006.01) |
| C08J 3/075 | (2006.01) |
| C08J 3/24 | (2006.01) |

(52) U.S. Cl.
CPC .. *C08J 3/24* (2013.01); *C08J 5/045* (2013.01); *C08J 3/075* (2013.01); *C08J 2329/04* (2013.01); *C08J 2205/022* (2013.01); *C08J 2201/024* (2013.01); *C08J 9/26* (2013.01)
USPC ......... 428/304.4; 428/319.7; 264/41; 264/42; 521/61; 521/64; 521/151

(58) Field of Classification Search
USPC ........... 428/304.4, 319.7; 264/41, 42; 521/61, 521/64, 151
See application file for complete search history.

(56) References Cited

U.S. PATENT DOCUMENTS

| | | |
|---|---|---|
| 2,609,347 A | 9/1952 | Wilson |
| 3,998,215 A | 12/1976 | Anderson et al. |
| 4,663,358 A | 5/1987 | Hyon |
| 4,851,168 A | 7/1989 | Graiver |
| 5,336,551 A | 8/1994 | Graiver |
| 5,422,050 A | 6/1995 | Graiver |

*Primary Examiner* — Victor Chang

(57) ABSTRACT

Reinforced, laminated, impregnated, and materials with composite properties as cross linked polyvinyl alcohol hydrogel structures in bulk or cellular matrix forms that can take essentially any physical shape, or can have essentially any size, degree of porosity and surface texture. They have a wide range of physical properties, unusual and unique combinations of physical properties and unique responses to stress fields, which allows for their use in many end use applications.

2 Claims, No Drawings

REINFORCED, LAMINATED, IMPREGNATED, AND COMPOSITE-LIKE MATERIALS AS CROSS-LINKED POLYVINYL ALCOHOL HYDROGEL STRUCTURES

This application is a Continuation-in-Part application of U.S. patent application Ser. No. 10/963,053, filed Oct. 12, 2004, now abandoned, which is a divisional application of U.S. patent application Ser. No. 10/020,785, filed Oct. 29, 2001, now U.S. Pat. No. 6,855,743, from which priority is claimed.

The invention disclosed herein deals with reinforced, laminated, impregnated and composite-like materials as cross linked polyvinyl alcohol hydrogel structures in bulk (non-cellular) or cellular matrix forms that can take essentially any physical shape, or can have essentially any size, degree of porosity and surface texture. They have a wide range of physical properties, unusual and unique combinations of physical properties and unique responses to stress fields, which allows for their use in many end use applications.

BACKGROUND OF THE INVENTION

Polyvinyl alcohol and its hydrogel forms have a relatively long history of use in a wide variety of applications. Polyvinyl alcohol in the form of fibers and covalently cross linked polyvinyl alcohol sponges and foams have already established themselves as very useful materials in numerous applications such as in packaging, thermal and acoustic insulation, construction, furniture, transportation aerospace, food industry, household, textile, medical, cosmetics, and a number of other areas, For example, polyvinyl alcohol sponges are used commercially as filters for water, air filters in intakes of compressors, engines, and air conditioners, oil filters, and the like. Large numbers of uses of polyvinyl alcohol sponges are based on their ability to readily absorb and hold water such as, household sponges, absorbent cloths, industrial dehydrating rollers, paint rollers, acoustic filters, and the like. Polyvinyl alcohol in the form of fibers is also used in a wide variety of applications.

The use of polyvinyl alcohol hydrogels in the medical field is especially important because of the physico-chemical properties of the hydrogels. When the hydrogels are physically cross linked, they have exceptional compatibility with human and animal tissue. Some of the unique properties of physically cross linked hydrogels is that they are imperviousness to attack by body fluids, blood, urine and other bodily secretions. They are non-sticking and non-adherent to tissue, essentially they do not have an affinity for sticking to proteins and they do not have cell adsorption. They are non-thrombogenic and have exceptional biocompatibility.

There are basically two families of methods for the preparation of bulk and cellular hydrogels, that is, one method which relies on covalent cross linking and the other method which requires physical cross linking of the polyvinyl alcohol molecules.

Thus, covalent cross linking, also known as chemical cross linking, includes the use of multi-functional reactive chemical molecules such as aldehydes, maleic acid, dimethyl urea, di-isocyanates, boric acid, and the like, and also the use of ionizing radiation, ultraviolet light, and the like, while physical cross linking methods, also known as reversible cross linking, includes cross linking through crystallites, hydrogen bonding and complexing agents such as titanium, aluminum, manganese, and copper, to name a few. Physical cross linking through formation of crystallites in polyvinyl alcohols has been reported, using for example, partial freeze-drying, repeated freezing and thawing, low temperature crystallization, physical cross linking induced by the presence of aqueous solutions of organic compounds, salts, acids and bases and the like.

Porous (cellular) polyvinyl alcohol materials have been prepared by frothing methods and the only method known to the inventor herein is the preparation of cellular polyvinyl alcohol hydrogels using covalently cross linked polyvinyl alcohol matrices. Physical cross linking methods have been reported only for the preparation of bulk polyvinyl alcohol hydrogels.

The preparation of cellular polyvinyl alcohol hydrogels having open pores by reacting polyvinyl alcohol with formaldehyde in an aqueous solution has been known for a long time. The earliest disclosure of a method can be found in U.S. Pat. No. 2,609,347, which issued to Wilson in 1952, that teaches the preparation of porous polyvinyl alcohol hydrogels by cross linking the hydrogels with formaldehyde at temperatures between 20° C. and 60° C. in the presence of an acid catalyst, such as sulfuric acid. Porous structures are created by entrapping gas bubbles in the polyvinyl alcohol solution in the presence of wetting agents that stabilize the bubbles and help to disperse the bubbles uniformly throughout the polyvinyl alcohol phase. The first step in the preparation of those hydrogels is the preparation of a solution of the polyvinyl alcohol or its copolymers in appropriate solvent, typically water. Then the entrapment of the air bubbles in the polyvinyl alcohol solution in the presence of a surfactant is carried out and finally, the polyvinyl alcohol is cross linked by reacting it with a multi-functional cross linker.

The cross linking agents used in the prior art processes render the polyvinyl alcohol sponges insoluble in any solvent due to formation of the covalent bonds between the molecules. Typically, cross linking agents for the hydrogels are selected from the aldehyde family such as for example, formaldehyde, glyoxal, gluteraldehyde and others that leads to the formation of highly acetalized cellular networks.

The only method for the preparation of cellular polyvinyl alcohol hydrogels by a pore forming method is that based on chemically cross linked matrices. The inventor herein is not aware of any reported method for the preparation of physically cross linked cellular polyvinyl alcohol hydrogels using pore forming methods.

Bulk polyvinyl hydrogels can be prepared by a number of methods. These methods teach gelling of the hydrogels from their solutions, by, for example, cooling the solution, or by addition of gelling agents such as, for example, phenol, naphtol, Congo Red or amino or metallic compounds. Initially, only aqueous solutions were used and were gelled by cooling to room temperature or below 0° C. Such hydrogels are invariably fragile, weak, sticky and unstable in water. A number of methods have also been reported to enhance the properties of such hydrogels. Almost every time, it was attempted by inducing additional chemical cross links using aldehydes, boric acid, radiation and coordination bonding. However, none of the methods that generate chemical bonds was successful in sufficiently enhancing the physical properties of the hydrogels.

A major improvement in the performance characteristics of the hydrogels is disclosed in U.S. Pat. No. 4,663,358 that issued to Hyon in 1987. This patent discloses a method of manufacturing polyvinyl alcohol hydrogels by cooling a solution of the polyvinyl alcohols to below 0° C. in a mixed solvent consisting of water and a water-miscible organic solvent. The preferred solvent is a mixture of water and dimethylsulfoxide, with the water concentration being in the range of from 10 to 90 weight percent. The hydrogels prepared from mixed solvents are transparent whereas hydrogels prepared from the solution in either water or dimethylsulfoxide as the only solvent, are opaque.

U.S. Pat. No. 4,851,168 that issued in 1989 to Graiver teaches a method of preparation of hydrogels and in particular polyvinyl alcohol fibers, by cooling a non-aqueous solution of polyvinyl alcohol to below −10° C., wherein the solvent is a mixture of monohydric alcohols containing 1 to 4 carbon atoms and dimethylsulfoxide. The preferred concentration of mixed organic solvents is about 10 to 30 weight percent of a monohydric alcohol and the rest being dimethylsulfoxide.

A review of the prior art has disclosed that no references were found for laminated structures or for a structure with composite or composite-like properties, or for impregnated structures of physically cross linked bulk polyvinyl alcohol hydrogels.

Two patents, U.S. Pat. No. 5,336,551 that issued to Graiver in 1995, and U.S. Pat. No. 5,422,050 that issued to Graiver in 1994, teach the composition of matter and the method to reinforce bulk polyvinyl alcohol hydrogels by increasing the degree of crystallinity of PVA hydrogels by imbedding externally preformed crystallites of desired size, shape and aspect ratio In the hydrogels. Column 2, line 65 states that "The objective of the invention is to provide a method for introducing highly crystalline regions into a polyvinyl alcohol hydrogel. The regions function as reinforcing agents for the hydrogel". This is a very key statement in Gravier's patent. That statement reflects exactly what they have done to improve the tensile properties of PVA hydrogel matrices, that is, by dissolving PVA fibers starting from the outer surface. These treated PVA fibers are imbedded into the PVA hydrogel matrix and fibers become an integral part of the matrix without any identifiable boundaries between the fibers and the hydrogel matrix. In fact, crystalline regions of the fiber become crystalline domains in the new PVA hydrogel matrix. These crystalline regions join the crystallites that have been created in the PVA hydrogel as physical crosslinking sites. They simply increase the degree of crystallinity of the PVA hydrogels.

The reinforcement is accomplished by uniformly dispersing a plurality of fibrils made from highly oriented crystalline polyvinyl alcohol, wherein the diameter of the fibrils is less than 1 mm and the aspect ratio of the fibrils is from 2:1 to 1000:1. The key feature of a reinforced hydrogel material made according to this invention is that it has a gradual transition in the degree of the crystallinity at the interface between the matrix and the fibrils.

As opposed to the prior art structures, the structures of the invention disclosed herein require no prior treatment of the polyvinyl alcohol fiber to establish strong interfaces between the fibers and the hydrogel matrix. This leads to cohesive failure as the only failure mechanism of the reinforced polyvinyl alcohol hydrogels. The imbedded PVA fibers used for reinforcement never become an integral part of the PVA hydrogel matrix but remain and retain their own identity all the time while imbedded into the PVA hydrogel matrix. Also, the present invention requires no pretreatment of a number of other fibers or structures used to reinforce and/or laminate such hydrogels, such as, silk, wool, cellulose, acrylates, carbon, graphite, and the like. The simple addition of these fibers or structures to the polyvinyl alcohol solution prior to gellation or crystallization will provide sufficiently strong interfaces with the hydrogel and thus, ensure no adhesive failures of the structures set forth herein.

By the invention herein, there is provided methods by which a material with composite-like structures can be obtained by combining physically cross linked bulk or cellular polyvinyl alcohol hydrogels with other materials and their structures. One can also combine physically cross linked bulk or cellular polyvinyl alcohol hydrogels with covalently cross linked polyvinyl alcohol hydrogels and arrive at unique unitary structures capable of providing adhesive strength. Such adhesive resistance, wherein any failure is due to cohesive failure, indicates that the interfacial bonding strength is higher than the strength of the polyvinyl alcohol hydrogel itself.

Thus, in summary, the prior art teach the use of polyvinyl alcohol fibrils to reinforce bulk polyvinyl alcohol hydrogels. The method of the prior art requires heating the fibrils in a solvent for a certain time periods to soften and partially dissolve the surfaces of the fibrils that is necessary to impart strong interfaces between the fibrils and the hydrogel. This method is cumbersome and is difficult to use because of the difficulties in defining the exact time necessary to soften the fibrils without over-softening them. Furthermore, any upset in the process parameters, especially an increase in the solvent treatment temperature, or exposure to the solvent for too long a period of time, will lead to excessive or even complete dissolution of the fibrils.

THE INVENTION

The invention disclosed and claimed herein deals with reinforced, laminated, impregnated, and materials with composite or composite-like properties as physically cross linked, bulk and cellular polyvinyl alcohol hydrogels. The structures disclosed herein are highly resilient without breaking or tearing, are hydrophilic, not affected by common organic solvents, not affected by changes in pH, or extremes of pH, are resistant to microbial attack, are highly biocompatible, are non-toxic, are lint free, and are free of any foreign leachable or covalently bonded materials.

It is an object of this invention to provide a method for the preparation of reinforced, or laminated, or materials with composite-like properties, or impregnated, unitary articles or structures that are composed of combinations of physically cross linked bulk and/or cellular polyvinyl alcohol hydrogels having different physical properties either alone or in combination with reinforcement and/or lamination and/or materials with composite or composite-like properties, and/or impregnated structures.

It is another object of this invention to provide reinforcement and/or lamination and/or materials with composite or composite-like properties, and/or impregnated structures which can be combined with polyvinyl alcohol hydrogels to produce systems having a wide variety of physical properties such as, desirable modulus, porosity, water content, water uptake ability, and the like, that can result in articles having almost any desired combination of physical properties and performance characteristics.

Yet another object of this invention is to provide processes to tailor physical properties of reinforced and/or laminated and/or materials with composite or composite-like properties and/or impregnated polyvinyl hydrogel compositions by selecting proper molecular parameters of polyvinyl alcohol polymers and solvents, porosity, texture, water content, water uptake ability, and the like, of cellular and bulk polyvinyl alcohol hydrogels and, selecting the proper type of reinforcing agents and/or laminating structures, and/or a material with composite properties structures, and/or impregnated structures, and/or mixtures of polyvinyl alcohol hydrogels with other more or less hydrophilic materials, and by selecting processing conditions for solvent treatment and heat treatment to provide articles of exceptional character and physical properties.

Still another object of this invention is to provide methods of coloring and/or making polyvinyl alcohol hydrogel compositions and articles Radio opaque and to provide methods of complexing such polyvinyl alcohol matrices with iodine and/or other germicidal agents or disinfectants that can be fashioned into useful articles or structures.

The physical properties of the structures of this invention can be widely varied and precisely tailored to the needs of the particular end use application by controlling the molecular and processing parameters, choosing the appropriate type of hydrogel, i.e. cellular, bulk, or a combination of these, and the nature and the form of reinforcing agents, laminating agents, a material with composite or composite-like properties, and impregnating agents and structures, and the like. The hydrogel structures have an unusual combination of physical properties as well as an unusual response to compressive and extensional stress fields, low to exceptionally high water holding capacity, slow to nearly instantaneous water wicking abilities, low to exceptionally high compressibility and expandability, weak and delicate in one dimension to exceptionally strong in another dimension in the same object, weak and delicate in one dimension while having high modulus and tear resistance in another dimension in the same object, non-abrasive and very slippery, to significantly abrasive and rugged exteriors.

The hydrogel structures of this invention can be colored or dyed, can be made Radio opaque or complexed with iodine and other germicides and disinfectants.

The hydrogel structures of this invention can be subjected to a solvent treatment and/or heat treatment subsequent to gellation in order to modify and further tailor their physical properties.

The term "bulk polyvinyl alcohol hydrogel" as used herein means polyvinyl alcohol hydrogels that have a certain size, shape and volume, and are recognizable as one, two or three-dimensional bodies, i.e. fiber-like, sheet-like or three-dimensional objects that are non-cellular, that is, being macroscopically non-porous bodies.

"Hydrogel" as used herein means bulk (i.e. macroscopically non-cellular) or cellular (i.e. sponge or foam-like) polyvinyl alcohol hydrogels that contain water but are not soluble in water at temperatures below 40° C.

"Composite" as used herein means both composites and structures having composite properties.

"Lamination" is defined herein for purposes of this invention as a placement or imbedding in polymer matrices, long continuous fibers in the form of strand, mats, woven, non-woven structures/textiles, various braided structures, etc. "Lamination" does not include the use of short fibers, but fibers that for all practical purposes can be considered to be continuous throughout the length of polymer matrix or fibers that have a significant overlapping along the fiber length such as in ropes and mats which is not possible to do with short or chopped fibers that are used in reinforcement of polymer matrices as shown in the prior art.

The polyvinyl alcohol hydrogels of the present invention can be designed to have exceptionally wide ranges of physical properties and can have unusual combinations of properties within the same unitary structure or article. This can be accomplished according to this invention by selecting and controlling molecular and processing parameters, selecting the nature and the form of reinforcing and/or laminating and/or a material with composite properties, and/or impregnated structures, selecting and combining hydrogels having certain desirable modulus, porosity, surface texture skin or lack thereof, water content, water uptake ability and the like.

For example, unitary structures or article or blocks of materials can have a multitude of properties such as the following. They can be prepared by combining into one unitary structure, polyvinyl alcohol hydrogels having different physical properties such as, porosities and/or Modulii and/or responses to stress fields, water content, water uptake abilities, and the like. One section of a structure, or article may contain some reinforcement and or lamination and another section of the same article may not. For example, one section or one side of a structure can be bulk polyvinyl alcohol hydrogel having one set of desired physical properties while the other section or side can be cellular polyvinyl alcohol hydrogel having another set of desired physical properties. One section or one side of a structure may consist of cellular polyvinyl alcohol hydrogel having one type and degree of porosity and one set of physical properties while the other side or section may have a different type and/or degree of porosity and the same or different set of physical properties. Each side may or may not have a skin. One dimension/direction/surface of an article can be soft, delicate, slippery, while another dimension/direction/surface can be hard, tough, rugged, abrasive, high modulus, tear resistant, and the like. One can have a surface or section of an article reinforced and/or laminated and/or combined with other types of materials into materials with composite properties while the other surface or section of that article can be bulk or cellular polyvinyl alcohol. One can have one surface or section of an article with a polyvinyl alcohol of one modulus while another surface or section may have a widely differing modulus.

One can curl, twist, bend, ripple, or warp, or change shape in a reproducible and controlled manner induced by a loss or gain of water or other hydrophilic liquids. The extent and direction of curling, twisting, rippling, warping, and bending of an article can be controlled by imbedding single or multiple, high modulus or elastomeric fibers, sheets, laminates, or any other such desired structure, or by combining a neat polyvinyl alcohol hydrogel on one side with reinforced or laminated polyvinyl alcohol hydrogel on the other side. Also, the article can be composed of two or more different hydrogels placed on different sides of the article. One side can be neat polyvinyl alcohol hydrogel while the other side of the article can be a combination i.e. a mixture of polyvinyl alcohol hydrogels with super absorbers such as sodium acrylate or sodium alginate and the like, or components which reduce water uptake ability of the hydrogel such as, poly(vinyl pyrrolidone), and the like.

The hydrogel structures of the present invention can also be colored, dyed, or rendered radio opaque and/or impregnated with disinfectant dyes and or complexed with iodine and/or other germicides.

These materials can be incorporated into the hydrogels either by homogeneously or heterogeneously dispersing them therein. They are useful during surgery. The radiopacity permits a surgeon to easily locate the bulk or cellular material that has been placed into a body cavity, visually, or by X-Ray. Radio opaque-containing materials can also be placed at certain designated locations in a device to assist in visual guidance and positioning of a device, such as in the case of an aneurysm treatment.

Typical Radioopaque materials are those having high electron density and include, but are not limited to barium sulfate, bismuth suboxide, gold, and the like. Radioopaque materials are added in various amounts to the hydrogels, usually at the level of from about 1 to about 35 weight percent based on the total weight of the additive and the hydrogel.

The hydrogels of this invention can be plasticized and thus can be made permanently flexible. This can be accomplished by incorporating suitable plasticizers, such as, but not limited to, polyhydric alcohols having 2 to 6 carbon atoms and 2 to 3 hydroxyl groups, particularly alkane diols and triols, diglycols, triglycols, polyethylene and polypropylene glycols of various molecular weights and mixtures thereof. The use of triethylene glycol is especially preferred for plasticization of the hydrogel matrices when the articles are intended to be used for topical human applications, and glycerin is generally used when the plasticizer needs to have low cytotoxicity.

Physical properties of bulk and cellular physically cross linked hydrogels can be significantly improved by reinforcing and/or laminating agents and/or impregnating agents or structures through the formation of sufficiently strong interfaces between the hydrogel matrix and reinforcing and/or laminating and/or impregnating agents or structures and/or materials with composite properties so that preferentially adhesive failure is eliminated in such a system, or, through the formation of sufficiently strong mechanical interlocking between the hydrogel matrix and reinforcing agents and/or laminate structures and/or materials with composite structures, and/or impregnated structures, or through a combination of these methods, which provide significant improvement in mechanical properties of the overall systems.

Unitary articles composed of polyvinyl alcohol hydrogel sections/sides having different compositions, modulii, porosity, surface texture, water content, water uptake ability, and the like, can be prepared generally in the following manner, with the details of such methods being set forth infra.

For example, one can prepare different concentrations of solutions of the polyvinyl alcohol or use different molecular weights of polyvinyl alcohols for preparation of solutions, provided that each solution can generate hydrogels having different but desirable physical properties such as, water content, water uptake ability, and the like, and then combine them in a mold, or in some other method, simultaneously or sequentially, or combine them with covalently cross linked polyvinyl alcohol bulk/sponge/foam hydrogels.

One can prepare cellular polyvinyl alcohol hydrogels by either pore forming methods or frothing methods either simultaneously or sequentially and combine them with bulk physically cross linked polyvinyl alcohol hydrogels or with covalently cross linked polyvinyl alcohols to create portions of an article having different porosities, different physical properties, which may have skin or no skin, and the like.

One can coat or cover, in any desired manner, reinforced and/or laminated and/or impregnated and/or materials with composite properties, covalently cross linked polyvinyl alcohol structures with either neat polyvinyl alcohol solution or with any desired mixture of polyvinyl alcohol with other materials and subject such systems to conditions which will induce formation of physical cross linking sites in the polyvinyl alcohol matrix.

One can prepare a block from any PVA hydrogel material having desirable dimensions, shape and composition, and then machine the final article out of that block material, either at room temperature or by first freezing the whole block of material in the form of the hydrogel and then machining an article from the frozen block.

One can prepare a polyvinyl alcohol solution by mixing the polyvinyl alcohol with superabsorbing materials or materials which reduce the ability of the materials to absorb water, and make bulk and/or cellular polyvinyl alcohol hydrogels and use them to make any combinations or articles described above.

Following is a general outline of the steps required to make the structures and articles of this invention.

A. The polyvinyl alcohol polymers are first dissolved in single or mixed solvents.

B. The appropriate conditions for preparation of the polyvinyl alcohol hydrogels are then selected according to the desired modulus and/or degree of porosity, water content, water uptake ability, and other physical properties of cellular and/or bulk polyvinyl alcohol hydrogel matrices and/or mixtures of polyvinyl alcohols with other more or less hydrophilic materials.

C. Mixing or otherwise combining the desired polyvinyl alcohol solution with reinforcing agents and/or laminating and/or impregnating structures and/or colorant and/or disinfectant dyes and/or any other adjuvants desired for making hydrophilic materials and/or any other adjuvant for making a particular type of bulk or cellular polyvinyl alcohol hydrogel matrix and/or coating or covering desired structures with the hydrogel solutions or hydrogel mixtures.

D. Combining the material obtained in C with one or more neat polyvinyl alcohol hydrogels having desired physical properties, or mixture of such hydrogels with any ingredient listed in C, including mixtures of polyvinyl alcohol with other superabsorbing hydrogels or components which can increase or reduce water uptake ability of the hydrogels.

E. Generating physical cross linking in the hydrogel matrix by using any of the known methods that lead to formation of crystallites and/or hydrogen bonding of the molecules leading to gellation and/or coagulation of the polyvinyl alcohol matrix.

F. Removing substantially all of the solvent used to make B or C by either evaporation, extraction or by any other means which does not substantially affect the polyvinyl alcohol cross linking sites or the components of the mixture of B and C G. Solvent treating or heat-treating the article or material, when desired, at elevated temperatures for a certain period of time in a non-oxidizing environment.

H. Washing the hydrogel with water when necessary and re-hydrating the hydrogel.

When the articles are prepared that contain cellular polyvinyl alcohol hydrogels, it is typically desirable to follow all of the steps from A to H. However, when bulk polyvinyl alcohol hydrogels are a component of an article, the steps F and G are typically omitted because the properties of these hydrogels can be or are better tailored in other ways such as, by selecting proper polyvinyl alcohol concentrations, molecular and processing parameters, and the like, that are known in the art of physically cross linked polyvinyl alcohol bulk hydrogels.

The instant invention also includes a combination of bulk and cellular physically cross linked polyvinyl alcohol hydrogels with covalently cross linked polyvinyl alcohol hydrogels and their combinations with reinforcing and/or laminating and/or materials with composite properties and/or impregnated structures into articles having desirable compositions and physical properties.

Thus, the first step in the preparation of polyvinyl alcohol hydrogels according to the present invention, is the preparation of the appropriate polyvinyl alcohol solutions by dissolving polyvinyl alcohol polymers in a single or mixed solvent, such as, water, non-aqueous organic solvents, mixed organic solvents, or aqueous solutions of salts, acids or bases.

The preferred average degree of polymerization of polyvinyl alcohol polymer is above 500. Typically, the higher the degree of polymerization of polyvinyl alcohol polymer, the more desirable are the mechanical properties of the hydrogels. Polyvinyl alcohol polymers with degrees of polymerization lower than 500 can also be used to make cellular hydrogels according to this invention, however, such hydrogels may not have sufficiently good mechanical properties, especially at low polymer concentrations, unless they are subjected to a post treatment, such as solvent or heat treatment. The preferred degree of hydrolysis of the polyvinyl alcohol is eighty-eight percent or higher. If the hydrogels having high strength, high tear resistance and stability to hydrophilic solvents are desired, then a preferred degree of hydrolysis is greater than ninety-five percent, and most preferred is fully hydrolyzed polyvinyl alcohol. The preferred degree of branching of the polymers is no branching at all, or a minimum of branching.

The concentration of the polyvinyl alcohol in solution, for purposes of this invention, is preferred to be between 0.5 and 50 weight percent, but it is not so limited. The preferred concentration will depend on the degree of polymerization, degree of hydrolysis, desired properties of the resulting hydrogels, the nature of the method used to induce physical cross linking, the nature and the extent of post treatment and the like.

The bulk and cellular hydrogels of the present invention can be reinforced with long fibers, woven and non-woven, one dimensional, two-dimensional or three-dimensional fibrous or non-fibrous structures without pre-treatment of reinforcing material. These hydrogels can also be laminated with and/or can impregnate or coat the same variety of materials and structures as in the case of reinforcement, and lamination. Also, the hydrogels having widely different modulii, porosity, water content, water uptake ability, and the like can be combined into a unitary article by combining their solutions in any desired manner, either in a one step or a multiple step method, simultaneously or in a sequence. Furthermore, reinforced and/or laminated, and/or a material with composite properties hydrogels, or articles impregnated with such hydrogels having different physical properties can be combined into a unitary article either in one, or two or more steps. Still further, any of the above-mentioned hydrogels can be further combined with other hydrogels and materials of any shape, size or structural complexity to make articles having even more complex, but desirable combinations of properties.

Materials having non-polar surfaces can also generate reasonably strong interfaces provided that their surfaces have been modified or functionalized so that they can have sufficiently strong interaction with the polyvinyl alcohol hydrogel. An example would be a modified surface of a polyolefin polymer such as Vectra® fibers available from Hoechst Celanese Corporation of Charlotte, N.C., USA. Surface modification of non-polar substrates is typically done by discharge treatments (corona, and glow discharge), flame, ozone, radiation, or wet treatment. The wet treatment of fiber surfaces requires the use of reactive chemical agents such as those used to make primers, coatings, electrodeposition, grafting, and the like. The laminate and the reinforcement and impregnating material can also be based on naturally occurring or man made fibers, non-woven fabrics of naturally occurring or man made fibers, strands of naturally occurring and man made fibers, knitted structures of naturally occurring or man made fiber, and the like.

High strength and high modulus polyvinyl alcohol hydrogel composites, and/or reinforced and/or laminated, and/or impregnated articles are obtained especially when long fibers are woven or knitted into two-dimensional or three dimensional structures which are subsequently encapsulated and/or impregnated with polyvinyl alcohol hydrogels. Mechanical strength of such structures will be the function of fiber orientation, number of fibers per cross sectional area and the extent to which the fibers are stretched or aligned in the structure. Mechanical properties of such hydrogel structures can be conveniently tailored by using appropriately oriented fibrous structures and by choosing the appropriate type of weaving, knitting, or braiding which will define the direction of the mechanical reinforcement. Fibers used to weave or knit or braid the fabrics can be of the same kind or blended fibers of different kinds and origins. In the cases of an extensional force field, the fibers and structures are actually load bearing while the hydrogel matrix holds the fiber/fibrous structures together and provides a means to maintain form and shape of an article. When such composites are subjected to compression, the response of the material with composite properties will typically be that of the hydrogel matrix itself. Typically, the contribution of the fibrous structure in compression is not that significant. Fibers useful herein can be naturally occurring or man made fibers, polymer foams, metals, ceramics, polymers, and the like. All of the reinforcing, laminating and impregnating fabrics and structures typically have an intra-fabric void ratio between 20 and 90 percent by volume.

Fibers useful herein include, but are not limited to, synthetic fibers such as polyethylene terephthalate (PET), polyethylene (PE), polypropylene (PP), nylon, polytetrafluoroethylene (PTFE), polyurethane (PU), polyvinyl alcohol (PVA), polyacrylates, rayon (regenerated cellulose fibers) and the like. Natural fibers can be for example, collagen, chitin, choitosan, and the like. Biodegradable fibers are, for example, PGA, i.e. poly(glycolic acid), PLA, i.e. poly(lactic acid), PLG, i.e. poly(lactic-co-glyclide) copolymers, PGL, i.e. poly(glycolide-co-lactide) copolymers, polydioxanone, and the like. Inorganic fibers include, for example, carbon fibers, ceramic fibers, hydroxyapatite, polysiloxane fibers, and the like.

The laminate or the mechanical support for the hydrogels can be made from woven or non-woven fabrics or films having plain, twilled, leno, and the like, weaving. The preferred laminate material has a porous, screen-like, fibrous or mesh structure. The most suitable supports for laminates are typically made from long fibers and include woven fabrics, non-woven fabrics, strands, strands of interconnected/knitted structures, or other interconnected fibrous structures, all either naturally occurring or man made.

Yet another embodiment of this invention is the provision of materials with composite properties from polyvinyl hydrogel structures having the capability of performing as semipermeable membranes which are useful, for example, in ultrafiltration and high-pressure separation processes. The semi-permeable membrane is composed of a porous support layer made from woven or non-woven fabrics. The fabric serves as reinforcement, a portion of a laminate, or an impregnating structure and is covered with a layer of the polyvinyl alcohol hydrogel resulting in an impregnated microporous membrane. Pre-sizing of the membrane openings can be a function of the polyvinyl alcohol hydrogel itself, or the size can be generated by a method of extraction of a pore forming material. In order to improve the interfacial strength between the polyvinyl hydrogel and the fabric, it is sometimes desirable to modify, for example, by corona treatment, the surface of the fibers used to make the fabric.

Another embodiment of the present invention is to prepare reinforced and laminated high strength, high modulus polyvinyl alcohol hydrogels and articles made from them, having exceptional dimensional stability in tension, but in compression, having properties essentially the same as those characteristics of bulk or cellular polyvinyl alcohol hydrogel itself. The reinforcement or lamination is accomplished by incorporating reinforcing or laminating agents or structures into polyvinyl alcohol hydrogels such as, knitted, woven or non-woven fabrics where fabrics were knitted or woven in three-dimensional networks which are subsequently impregnated or encapsulated with bulk or cellular polyvinyl alcohol hydrogels. The fibers of the three dimensional fabrics can be of natural, organic, inorganic or of man made origin. When three-dimensional weaving is done by tri-axial weaving, it can lead to the formation of tubular woven or knitted structures that can be impregnated or laminated with the bulk or cellular hydrogels. Such impregnated or laminated structures are useful as artificial blood vessels, catheters, hoses, tubes, and are especially useful to make articles and devices that are in contact with blood or other body fluids because of exceptional anti-thrombogenic and other biocompatibility properties of the hydrogels. Another application of impregnated and laminated three dimensionally woven structures is the use as an artificial ligament, especially when it is made in the form of a cord.

Another embodiment of the present invention is when the reinforcement or laminate is inserted through the axis of a cylinder or through different symmetry axes of an geometrical article or through any direction of a three dimensional or a two dimensional article made from a bulk or cellular polyvinyl alcohol hydrogel. One can use filaments, ropes, roving, non-woven or woven long fibers in one dimension or two dimensions or even three dimensions to control the expansion of the impregnated polyvinyl alcohol hydrogel-based article. This provides directional stability and control of directional expansion, curling, twisting, bending, warping, and the like. This is possible because fibers have either sufficiently good interfacial strength with the hydrogel, or are sufficiently well mechanically interlocked with the hydrogel, to prevent, reduce, or control completely, or partially, or differentially, the extent of expansion of the hydrogel in the desired direction upon loss or gain of liquids, such as water, or hydrophilic liquids, or, when the hydrogel is exposed to a stress field.

Yet another embodiment of the present invention is to produce hydrophilic bulk or cellular polyvinyl alcohol hydrogel matrices free of any reactive additives and any dangling, non-reacted functional groups belonging to covalent type cross linkers or surface modifiers or any other additive. These materials are obtained by physically cross linking through crystallites and hydrogen bonding, wherein crystallites may also serve as reinforcing agents. These structures provide exceptional mechanical properties, environmentally degradable, lint free, even when cut and used abrasively, flexible, compressible and resilient, properties. They have a remarkable ability to retain their original shape and volume after a force has been removed that has been applied to them that has been used to drain the free water from the pores thereof. They are useful in a wide variety of applications including household, cosmetic, transportation, biomedical and numerous other applications. Since the polyvinyl alcohol hydrogel matrices of this invention are physically cross linked, they can be dissolved at or near the boiling point of water or in other appropriate solvents for the polyvinyl alcohol, and provide desirable routes for disposal and recycling of the articles having bulk and cellular polyvinyl hydrogels as their matrix.

The cross linking of the polyvinyl alcohol solutions leading to bulk or cellular hydrogels can be accomplished by subjecting the solutions or mixture to any of the following:

Simple cooling below 130° C., or
single freezing and thawing, or
repeated freeing and thawing in cycles, or
freezing and then partial or complete freeze drying, or
applying conditions that induce physical cross linking such as the use of aqueous solutions of salts, acids or bases, or solutions of organic compounds, and the like.

Since some of these methods may produce relatively weak hydrogel matrices or hydrolytically unstable cross linking sites, it is advantageous to subject these hydrogels to a post treatment to improve the physical properties especially in the case of cellular hydrogels. However, when the hydrogels are dissolved in mixed solvents, such as those based on dimethylsulfoxide and water or dimethylsulfoxide and alcohol, the simple holding of the solutions at temperatures below about 130° C., or cooling the mixture to temperatures near or even below 0° C., tend to create remarkably strong physically cross linked hydrogel matrices. Post treatment of such hydrogel matrices is often not necessary except when it is desired to have hydrogel matrices having anisotropic physical properties or when the hydrogel matrix having exceptionally high mechanical strength, tear resistance, controlled elongation or collapsed cell walls are desired. Typically, in the case of cellular hydrogel matrices, the improvement of physical properties through the post treatment is often very desirable.

The present invention includes methods to tailor the physical properties of reinforced and/or laminated and/or a material with composite properties and/or impregnated structures made from them. All physical properties of these hydrogels can be varied widely by selecting appropriate processing conditions and molecular parameters of the polyvinyl alcohol and processing aids and desired post treatment.

For example, soft and delicate hydrogel matrices can be obtained by selecting polyvinyl alcohol polymers having lower molecular weight and/or lower degrees of hydrolysis and/or lower polyvinyl alcohol concentrations in solution. Solvent treatment is desirable when moderate improvement of physical properties of the whole article or the segment composed of only polyvinyl alcohol hydrogel matrix is desired. However, when physical properties of the hydrogels need to be significantly improved, such as, strength and tear resistance, the post treatment of the hydrogels, such as heat treatment is particularly desirable. The duration of heat treatment depends on the selected temperature and the nature of the media in which heat treatment is carried out. Typically, duration of the heat treatment is between 5 minutes to 12 hours or longer. The higher the heat treatment temperature, the shorter the required heat treatment time. The higher the heat treatment temperature, and the longer the duration of the heat treatment, the stronger the hydrogel or corresponding PVA matrix.

Mechanical drawing, i.e. molecular orientation of hydrated hydrogels can also significantly improve mechanical strength, modulus, tear resistance, and the like, of the hydrogel. This kind of treatment is typically most desirable when geometry of the object permits drawing such as in the case of fibers, rods, and films, and the like.

Some of the reinforced and/or laminated polyvinyl alcohol hydrogel matrices of the present invention, that are obtained immediately after the polyvinyl alcohol matrix has been physically cross linked are relatively weak, especially when prepared from solutions having extremely low polyvinyl alcohol concentrations or using polyvinyl alcohols having a low degree of polymerization and/or low degree of hydrolysis. This is often the case with cellular polyvinyl alcohol hydrogels. Mechanical properties of such hydrogels can be improved by the treatment of the hydrogels by solvents. Solvents used to prepare the polyvinyl alcohol gel need to be removed by extraction or evaporation, or any other convenient means. The solvent extraction and the solvent treatment are typically done simultaneously by simply placing the hydrogel into a desired low boiling solvent such as, methanol, or ethanol, or acetone, to extract all of the solvents used to prepare the solution. In order to accelerate solvent removal, the use of Soxhlet-like extractors is preferred. Upon extraction of all original solvents used to prepare the hydrogel, the gel becomes significantly stronger. It was also found that a simple drying of the extracted gel at room temperature typically further improves the mechanical properties of the hydrogel upon re-hydration.

Once the original solvents that have been used to prepare the polyvinyl alcohol solution are removed and the hydrogel matrix has been dried, the mechanical properties of the hydrogels can be further dramatically improved by subsequent heat treatment at elevated temperatures. The present invention requires that in order to maximize the improvement of physical properties by heat treatment of the hydrogel matrix, substantially all of the solvents must be removed. The heat treatment is believed by the inventor herein to be an "annealing" process that causes an increase in crystallinity of the polyvinyl alcohol, but the inventor should not be held to such a theory. The increase in crystallinity reduces the ability of the hydrogels to hydrate and expand making such hydrogel matrices significantly more firm, rugged, and abrasive, leading to significant increases in mechanical strength.

The preferred heat treatment of the hydrogel matrix is carried out at temperatures between 40 and 180° C., preferably in a vacuum or non-oxidizing atmosphere such as nitrogen or non-oxidizing liquids such as silicone oils, organic solvents, solutions of salts, or the like. Heat treatment may also be carried out in air, but oxygen from the air may cause undesirable oxidative degradation of the polyvinyl alcohol at elevated temperatures. It is critical that the heat treatment temperatures be lower than the melting temperature or degradation temperature of selected polyvinyl alcohol and that all ingredients such as reinforcement, laminating and impregnating materials, colorants, radioopaque materials, and the like, are also stable at the selected heat treatment temperatures. The duration of the heat treatment depends on the selected temperature and the nature of the media in which the heat treatment is carried out. Typically, the duration of a heat treatment is between 5 minutes to 12 hours or longer.

The structures of the instant invention based on PVA hydrogels have substantial biocompatibility. They are not toxic, they will not cause inflammation of tissue, and they will not irritate tissue or encourage tissue growth into them. They will not adhere to a human tissue nor require adhesion prevention ointments such as petroleum jelly, which in itself could produce a foreign body reaction of the tissue.

PVA hydrogels are capable of allowing water and water soluble, low molecular weight compounds to pass through them. Such compounds are, for example, ammonia, common salts, uric acid, urea, creatinine, glucose, lactic acid and antibiotics. However, the passing of bacteria, yeasts and molds cannot take place through them. Therefore, in the event that sterile polyvinyl alcohol hydrogel matrices are exposed to non-aseptic environment, the contamination of the polyvinyl hydrogel matrix is only limited to the surface of the hydrogel. The hydrogel can be made aseptic again by sterilizing the surface by using ultraviolet light or ethylene oxide, propylene oxide, ozone, hydrogen peroxide, aldehydes, ethyl alcohol, isopropyl alcohol, or chlorohexidine, or the like, followed by washing with sterile water or saline.

The biocompatibility of these hydrogel systems provides that they have a wide range of applications in the biomedical field. They can easily be made to contain very low to very high water content and thus can easily match the water content of various tissues. They can be used externally or internally, such as, but not limited to, bandages applied to wounds, trauma treatment such as thermal and chemical burns, or as application to ulcers, lesions and surgical sites, or sanitary napkins, swabs, surgical aids, various implants, such as cardiovascular, orthopedic, reconstructive and cosmetic surgeries. As surgical aids, these hydrogels can be used to remove body fluids such as blood, serum, plasma, lymph fluid, spinal fluids, urine, sweat, bile juices, digestive fluids, blotters for incisions, and the like. They can be used to separate organs and absorb blood and other body fluids during internal surgery. The smooth surfaces provide little or no abrasion to even the most delicate tissues, such as the brain, while maintaining an anti-thrombic character. Separation of organs can be done using these systems that are in the form of films and sheets, which can be reinforced or laminated, impregnated, or in the form of a material with composite properties, to maintain the desired form and shape.

The polyvinyl alcohol structures of the present invention are also useful in alkaline and acidic environments because they have good resistance to these materials. These polyvinyl alcohol structures can also act as superabsorbents.

Another embodiment of this invention is the impregnation of microcellular polyester and polyether based cellular urethane foams and the like with the bulk or cellular polyvinyl alcohol hydrogels with the result that unique materials with composite properties and structures are obtained that retain the physical properties of the support material, but exhibit the biocompatibility of the hydrogel. Other base materials that can be used are, for example, cellophane, cellulose acetate, ethyl acetate copolymers, polyurethane, plasticized vinyl acetate-vinyl chloride copolymers, ethylene-vinyl acetate copolymers, polyester elastomers, polyether block copolymers, polyacrylates, ethylene-acrylate copolymers, polyesters, ionomer resins, nylon, polyethylene, polypropylene and their copolymers, polyvinyl chloride, paper, cloth, aluminum foil, and the like.

The polyvinyl alcohol structures of the present invention can have uses in endovascular, thoracic, gastrological and urological prosthesis applications. Such structures can be made by impregnating tubular, woven, three-dimensional fabrics, or crossed helical wire mesh structures, and the like. The tubular fabric can be woven in a tight manner providing no expansion, or can be woven in a manner that provides an ability to change the shape as a response to any stress field imposed on the impregnated tube and which can also act as a reinforcement that prevents the bursting of the tube. When the fabric is loosely woven and impregnated with the hydrogel, it can be used as an inflatable balloon. These structures can be used as stents, vascular grafts, catheters, expansion balloons, drainage tubes for body fluids, internal tubes that provide inner body secretions to flow from organs where they are produced to the desired organs, audio and pulmonary tubular structures, bandages and topical patches for wounds, burns, ulcers, lesions, trauma or surgical sites, transdermal films which can have the ability to release active agents into the body by targeting, triggering and modulating mechanisms of controlled release, suppositories which can have the ability for controlled release of active agents, and gauze-like pads.

The polyvinyl alcohol structures of the present invention can be used as substrates and/or scaffolding structures for tissue engineering. The substrates and scaffolding can be either made from neat bulk or cellular polyvinyl alcohol hydrogels or from the corresponding reinforced, laminated and/or impregnated and/or materials with composite properties in the form of one, two, or three-dimensional objects. They can be used as neat hydrogels or may contain any of the desirable bioactive agents that can be released in a controlled manner to induce, promote, guide, and the like, of tissue growth. These substrates and/or scaffolding structures made from polyvinyl alcohol hydrogels in addition to crystallite cross linking sites, may contain ionic cross linking sites that can be selectively removed leaving crystallite physical sites intact when desired. The selective removal of ionic cross linking sites is possible because of their hydrolytic instability in certain environments.

These structures also have application in non-surgical uses, for example, hydrogel sponges by themselves, or reinforced and/or laminated sponges with other, different materials, can be used in cosmetics and in health care application as absorbents and packing, and these sponges and laminated and reinforced sponges can be used in tissue protective applications such as catamenial pads, cardioplegic blankets, neurological sponges, bandages, dressing for wounds, and the like.

The polyvinyl alcohol structures of this invention can also bind disinfectants such as disinfectant dyes, such as methylene blue, gentian violet, acridine orange, brilliant green, acridine yellow, quinacrine, trypan blue, and trypan red, and the like.

The polyvinyl alcohol hydrogels can be used to modify the surfaces of other materials to provide structures having hydrophilic surfaces, biocompatibility, softness, slipperiness, and the like. These materials are particularly useful for biomedical applications such as for treating blood handling and blood testing equipment to prevent the adhesion of blood or blood components to the equipment, thus eliminating thrombogenic process that may cause false test results or make blood unsafe for patients to use.

The structures of this invention are useful as self-sealing gaskets and seals in applications that require special shapes, forms and performance characteristics, such as, for example, for handling water, or polar and non-polar solvents.

The technology of this invention is also useful in the manufacture of fishing lures, especially at the dockside, or in a boat, where the lures can be manufactured for the immediate need. These structures can also be formed into toys that have unique changes in shapes and sizes that are induced by the loss or gain of water.

They can take the form of films, tubes, rods, bulk pieces, which can be obtained by common methods such as extrusion, molding, casting, coating, machining, and the like. They can be co-extruded, co-molded, and co-cast, as well.

The fact that the hydrogels of the present invention can be produced by physical cross linking of the polyvinyl alcohol matrix and that the physical properties of the hydrogels can be modified and improved without the use of chemical means such as multi-functional cross linker or radiation or any other additives to create covalent cross linking sites, is a very desirable feature particularly when the hydrogels are used in biomedical application. Just as in the case of neat bulk and cellular hydrogels, the materials and the articles of the present invention, which include the reinforced, laminated, materials with composite properties, and impregnated articles from the hydrogels, possess all the desirable and unique properties of neat hydrogels plus some additional unique properties.

The ability to be reinforced and/or laminated, and/or make a material with composite properties, or make impregnated articles from bulk and cellular polyvinyl alcohol hydrogels having different modulus, response to stress field, porosity, water content, water, uptake ability, and the like is very important for a variety of applications. For example, such materials with composite properties can be very desirable to produce articles useful in medical applications, such as, wound and burn dressing, surgical aids, articles useful in dentistry, cosmetics and other applications as desired, wherein the unique hydrogel structures and articles are critical for the performance of the same.

Turning now to the methods by which the structures of the present invention are prepared, starting with the preparation methods for the polyvinyl alcohol solutions and hydrogels, one such method is the preparation of a cellular, physically cross linked polyvinyl alcohol structure, wherein the structure has a cross linked polyvinyl alcohol based matrix derived from a cellular cross linkable polyvinyl alcohol hydrogel wherein the cellular cross linkable polyvinyl alcohol based matrix is a hydrogel sponge having collapsed walls which have been prepared by a method comprising the steps of providing a polymer capable of being physically cross linked and then dissolving the polymer in a material selected from the group consisting essentially of a single solvent for the polyvinyl alcohol, or a mixture of solvents for the polyvinyl alcohol, to form a solution. The solution is then mixed with a pore-forming material. Then, the polymer is physically cross linked and this solution of cross linked polymer is brought to about room temperature and then essentially all of the solvents are removed by a method which does not significantly affect the cross linking or pore forming material. Thereafter, the mixture is heated at an elevated temperature for a period of from ten seconds to about eight hours and then cooled to about room temperature again and then the pore forming material is removed by a means which does not significantly affect the cross linking.

Yet another method is based on providing a physically cross linked polyvinyl alcohol based matrix derived from a cellular physically cross linkable polyvinyl alcohol hydrogel wherein the cellular physically cross linkable polyvinyl alcohol based matrix is a hydrogel sponge having expanded walls which has been prepared by the method comprising the steps of providing a polyvinyl alcohol polymer capable of being physically cross linked and dissolving the polymer in a material selected from the group consisting essentially of a single solvent for the polyvinyl alcohol or a mixture of solvents for the polyvinyl alcohol, to form a solution. This solution is then mixed with a pore-forming material and then physically cross linked. This material is then brought to about room temperature and the pore forming material is removed by a means which does not significantly affect the cross linking or pore forming material.

Still another method comprises providing a physically cross linked polyvinyl alcohol based matrix derived from a cellular physically cross linkable polyvinyl alcohol hydrogel wherein the cellular physically cross linkable polyvinyl alcohol based matrix has been prepared by the method comprising the steps of providing a polyvinyl alcohol polymer capable of being physically cross linked and dissolving the polymer in a material selected from the group consisting essentially of a single solvent for the polyvinyl alcohol or a mixture of solvents for the polyvinyl alcohol to form a solution. The solution thus formed is mixed with a pore-forming material capable of partially dissolving in the solution. There is then provided conditions at which the polymer will undergo physical cross linking caused by the presence of the partially dissolved pore forming material. The mixture is then brought to about room temperature and the pore forming material is removed by a means which does not significantly affect the cross linking or pore forming material.

In addition, there is another method which requires providing a physically cross linked polyvinyl alcohol based matrix derived from a cellular physically cross linkable polyvinyl alcohol hydrogel wherein the cellular physically cross linkable polyvinyl alcohol based matrix has been prepared by the method comprising the steps of providing a polyvinyl alcohol polymer capable of being physically cross linked and dissolving the polyvinyl alcohol polymer in a material selected from the group consisting essentially of a single solvent for the polyvinyl alcohol or a mixture of solvents for the polyvinyl alcohol to form a solution and then mixing the solution with a pore-forming material capable of partially dissolving in the solution. Then, providing conditions at which the polymer will undergo physical cross linking caused by the presence of the partially dissolved pore forming material and then bringing the mixture to about room temperature. Thereafter, all of the solvents are removed by a means which does not significantly affect the cross linking or pore forming material. Then heating the material at an elevated temperature for a period of time of ten seconds to about eight hours, and then cooling the mixture to about room temperature and removing the pore forming material by a means which does not significantly affect the cross linking.

A further method requires that there is provided a physically cross linked polyvinyl alcohol based matrix derived from a cellular physically cross linkable polyvinyl alcohol hydrogel wherein the cellular physically cross linkable polyvinyl alcohol based matrix has been prepared by a method comprising the steps of providing a polyvinyl alcohol polymer capable of being physically cross linked and dissolving said polymer in a material selected from the group consisting essentially of a single solvent for the polyvinyl alcohol or a mixture of solvents for the polyvinyl alcohol to form a solution and then mixing the solution with a pore-forming material. The mixture is then submersed in a bath consisting of a material selected from the group consisting essentially of a non-solvent for the polyvinyl alcohol polymer, or is a low temperature non-solvent for the polyvinyl alcohol polymer or, a poor solvent for the polyvinyl alcohol polymer, or an aqueous solution of a material selected from the group consisting essentially of a salt, or an acid at a low temperature, or, a base, to induce physical crosslinking such as crystallization, gellation, coagulation, or a mixture of crystallization, gellation, or coagulation, of the polyvinyl alcohol polymer. The solution is then brought to about room temperature and essentially all of the pore forming materials are removed by means which does not significantly affect the cross linking.

Going to still another method there is provided a physically cross linked polyvinyl alcohol based matrix derived from a cellular physically crosslinkable polyvinyl alcohol hydrogel in combination with a reinforcing material capable of reinforcing said matrix wherein the cellular physically cross linkable polyvinyl alcohol based matrix has been prepared by the method comprising the steps of providing a polyvinyl alcohol polymer capable of being physically cross linked and dissolving the polymer in a material selected from the group consisting essentially of a single solvent for the polyvinyl alcohol or a mixture of solvents for the polyvinyl alcohol to form a solution. The solution is mixed with a pore-forming material and reinforcing material and then submersed in a bath consisting of a material selected from the group consisting essentially of a non-solvent for the polyvinyl alcohol polymer at low temperature or, a non-solvent for the polyvinyl alcohol polymer, or a poor solvent, to induce crystallization, gellation, coagulation, or a mixture of crystallization, gellation, or coagulation, of the polyvinyl alcohol polymer.

The mixture is then brought to about room temperature and all of the pore forming materials are removed by a means which does not significantly affect the cross linking.

There is additionally provided a method that requires providing a physically cross linked polyvinyl alcohol based matrix derived from a cellular physically cross linkable polyvinyl alcohol hydrogel in combination with a reinforcing material capable of reinforcing said matrix wherein the cellular physically cross linkable polyvinyl alcohol based matrix has been prepared by the method comprising the steps of providing a polyvinyl alcohol polymer capable of being physically cross linked and dissolving the polymer in a material selected from the group consisting essentially of a single solvent for the polyvinyl alcohol or, a mixture of solvents for the polyvinyl alcohol to form a solution. The solution is then mixed with a pore-forming material and reinforcing material and then submersed in a bath consisting of a solution of a material selected from the group consisting essentially of a salt, or an acid at a low temperature or, a base to induce physical crosslinking such as crystallization, gellation, coagulation, or a mixture of crystallization, gellation, or coagulation, of the polyvinyl alcohol polymer. The mixture is then brought to about room temperature and essentially all of the pore forming materials are removed by a means which does not significantly affect the cross linking.

Yet another method requires providing a physically cross linked polyvinyl alcohol based matrix derived from a cellular physically cross linkable polyvinyl alcohol hydrogel in combination with a reinforcing material capable of reinforcing the matrix wherein the cellular physically cross linkable polyvinyl alcohol based matrix has been prepared by the method comprising the steps of providing a polyvinyl alcohol polymer capable of being physically cross linked and dissolving the polymer in a material selected from the group consisting essentially of a single solvent for the polyvinyl alcohol or, a mixture of solvents for the polyvinyl alcohol to form a solution. Thereafter, mixing the solution with a material selected from the group consisting essentially of a surface active agent or a mixture of surface active agents and frothing the mixture. Thereafter, mixing the froth with the reinforced material and cooling the frothed mixture to a temperature at which the polymer will undergo physical cross linking and then essentially removing any solvent present in the frothed mixture by a means which does not significantly affect the cross linking and then bringing the mixture to an elevated temperature for a period of time and then cooling the mixture to about room temperature.

Going on, there is provided still another method wherein there is provided a physically cross linked polyvinyl alcohol based matrix derived from a cellular physically cross linkable polyvinyl alcohol hydrogel in combination with a reinforcing material capable of reinforcing the matrix wherein the cellular physically cross linkable polyvinyl alcohol based matrix has been prepared by the method comprising the steps of providing a polyvinyl alcohol polymer capable of being physically cross linked and dissolving the polymer in a material selected from the group consisting essentially of a single solvent for the polyvinyl alcohol or, a mixture of solvents for the polyvinyl alcohol to form a solution. The solution is then mixed with a material selected from the group consisting essentially of a surface active agent or, a mixture of surface active agents and frothing the mixture. Thereafter mixing the froth with the reinforcing material and cooling the mixture to a temperature at which the polymer will undergo physical cross linking and then bringing the mixture to about room temperature.

Going to another method, the method requires that there is provided a physically cross linked polyvinyl alcohol based matrix derived from a cellular physically cross linkable polyvinyl alcohol hydrogel in combination with a reinforcing material capable of reinforcing said matrix wherein the cellular physically cross linkable polyvinyl alcohol based matrix has been prepared by the method comprising the steps of providing a polyvinyl alcohol polymer capable of being physically cross linked and dissolving said polymer in a material selected from the group consisting essentially of a single solvent for the polyvinyl alcohol or, a mixture of solvents for the polyvinyl alcohol to form a solution. Thereafter, mixing the solution with a material selected from the group consisting essentially of a surface active agent or, a mixture of surface active agents and frothing the mixture. Thereafter, mixing the froth with the reinforcing material and cooling the frothed mixture to a temperature at which the polymer will undergo physical cross linking and thereafter, submersing the mixture in a bath consisting essentially of a material selected from the group consisting of a non-solvent at low temperature for the polyvinyl alcohol or, a non-solvent for the polyvinyl alcohol or, a poor solvent for the polyvinyl alcohol or, an aqueous solution of a salt or, an aqueous solution of an acid at low temperature or, an aqueous solution of a base to induce crystallization, gellation, coagulation, or a mixture of crystallization, gellation, or coagulation of said polymer.

Still another method is that wherein there is provided a physically cross linked polyvinyl alcohol based matrix derived from a cellular physically cross linkable polyvinyl alcohol hydrogel in combination with a reinforcing material capable of reinforcing the matrix wherein the cellular physically cross linkable polyvinyl alcohol based matrix has been prepared by the method comprising the steps of providing a polyvinyl alcohol polymer capable of being physically cross linked and dissolving the polymer in a material selected from the group consisting essentially of a single solvent for the polyvinyl alcohol or, a mixture of the solvents for the polyvinyl alcohol to form a solution. Thereafter, mixing the solution with a material selected from the group consisting essentially of a surface active agent or, a mixture of surface active agents and frothing said mixture. Thereafter, mixing the froth with the reinforcing material and cooling the mixture to a temperature at which the polymer will undergo physical cross linking and thereafter, submersing the mixture in a bath consisting of an aqueous solution of a material selected from the groups consisting essentially of a salt or, an acid at low temperature or, a base to induce crystallization, gellation, coagulation or a mixture of crystallization, gellation or coagulation of said polymer.

There is also a method which requires providing a physically cross linked polyvinyl alcohol based matrix derived from a cellular physically cross linkable polyvinyl alcohol hydrogel in combination with a reinforcing material capable of reinforcing the matrix wherein the cellular physically cross linkable polyvinyl alcohol based matrix has been prepared by the method comprising the steps of providing a polyvinyl alcohol polymer capable of being physically cross linked and dissolving the polymer in a material selected from the group consisting essentially of a single solvent for the polyvinyl alcohol or, a mixture of solvents for the polyvinyl alcohol to form a solution and thereafter, mixing the solution with a material selected from the group consisting of a surface active agent or, a mixture of surface active agents and frothing the mixture and thereafter, combining the froth with the solution of polyvinyl alcohol containing a pore forming material and the reinforcing material into a unitary object of a desired shape and producing a material with composite properties. Thereafter, submersing the resulting a material with composite properties material in a bath consisting of a material selected from the group consisting essentially of a non-solvent for the polyvinyl alcohol or, a poor solvent for the polyvinyl alcohol and thereafter, providing conditions at which the polymer will undergo physical cross linking. Then bringing the mixture to about room temperature and removing the pore forming material by a means which does not significantly affect the cross linking.

Finally there is a method which requires providing a physically cross linked polyvinyl alcohol based matrix derived from a cellular physically cross linkable polyvinyl alcohol hydrogel in combination with a reinforcing material capable of reinforcing said matrix wherein the cellular physically cross linkable polyvinyl alcohol based matrix has been prepared by the method comprising the steps of providing a polyvinyl alcohol polymer capable of being physically cross linked and dissolving the polymer in a material selected from the group consisting essentially of a single solvent for the polyvinyl alcohol or, a mixture of solvents for the polyvinyl alcohol to form a solution. Thereafter, mixing the solution with material selected from the group consisting of a surface active agent or, a mixture of surface active agents and frothing the mixture and thereafter, combining the froth with a polyvinyl alcohol solution containing pore forming material and the reinforcing material. The combination is then submersed in a bath consisting essentially of a non-solvent for the polyvinyl alcohol or, a poor solvent for the polyvinyl alcohol and then providing conditions at which the polymer will undergo physical cross linking. Thereafter, the mixture is brought to about room temperature and the solvents are removed by a means which does not significantly affect the cross linking or pore forming material. Thereafter, heating the material at an elevated temperature for a period of time from ten seconds to about eight hours, and then cooling the mixture to about room temperature and removing the pore forming material by a means which does not significantly affect the cross linking. This method produces reinforced a material with composite properties objects consisting of two different cellular structures having collapsed walls.

It will be obvious to one skilled in the art upon reading this specification, to envision the possibility of variations, combinations and all of the possibilities of processing of the hydrogels and the reinforcement, lamination and impregnation of any object having a simple or complex composition, consisting of bulk and cellular polyvinyl alcohol hydrogel materials, once the essentials of this specification and the examples presented below have been studied.

For example, one can create the objects based on the enclosed teaching in the following general ways: making each section or segment of the object separately and independently of the other sections or segments, such that one section or segment is produced at a time, but in a continuous sequence of steps; making each section or segment of the object separately and independently of the other sections or segments, that is, one section segment at a time, and then assembling them later on and making them adhere to each other using, for example, warm or hot polyvinyl alcohol solutions, or tackifying the surfaces with solvents or using a cyanoacrylate types of glue or similar adhesives or, making all the sections or segments of the object simultaneously, i.e. at the same time by co-extrusion, co-molding, co-deposition, or using a process similar to ink-jet dispensing mechanisms for custom building of complex or intricate three-dimensional devices or objects, i.e. rapid prototyping or rapid stereo object production, relying on computer aided manufacturing.

The pore forming materials and surface active agents useful in this invention are those pore forming materials and surface active agents that are well-known to those skilled in the art, representative examples of which are set forth in the following examples.

EXAMPLES

Example 1

A polyvinyl alcohol polymer having a high degree of polymerization and having a viscosity of about 66 cps for a 4 weight percent aqueous polyvinyl alcohol solution at 20° C., and a high degree of hydrolysis of about 99.3% was dissolved in an 80/20 dimethylsulfoxide and water solution with the polyvinyl alcohol concentration at about 25 weight %. Dissolution was carried out at 120° C. under a nitrogen atmosphere while continuously stirring for three hours. Cotton gauze was placed on the entire bottom surface of a rectangular mold with the depth of the mold being about 4 mm. Then the solution, which had been kept at about 95° C., was poured on top of the gauze in the mold to completely fill the mold. Additional rectangular molds were used and the molds were filled with the solution to about half of the depth of the mold. Then, cotton gauze was placed on the top of the solution in the mold and an additional solution was poured into the mold to fill it. In both cases, the molds containing cotton gauze, together with the solution were placed into a freezer at a temperature of −18° C. for 8 hours. The molds were then taken out of the freezer and the reinforced matrices removed and submersed in a water bath to extract the dimethylsulfoxide. The water in the bath was changed four times every 6 hours. The resulting product contained no detectable dimethylsulfoxide. This hydrogel system had a high modulus, tensile strength and tear resistance along the plane of the cotton gauze, while perpendicular to the plane of the cotton gauze, the mechanical properties were those characteristic of the hydrogel itself. Upon a small loss of water, the hydrogel having gauze on only one of its surfaces curled uniformly onto itself. The hydrogel having gauze in the middle shrank uniformly upon controlled loss of water. When these reinforced and laminate samples were exposed to tensile or shear forces, they failed exclusively through cohesive mechanisms indicating that the interfacial strength between cotton gauze and the polyvinyl alcohol hydrogel matrix is at least as high as the strength of the polyvinyl alcohol hydrogel matrix itself.

Example 2

The same procedure was used as in example 1 except that the concentration of the hydrogel in the solution was five weight % and knitted wool cloth was used for the reinforcement. The surfaces of the reinforced hydrogel in this case were very soft and delicate to the touch. However, modulus, tensile strength and tear resistance in the plane of the reinforcement corresponded to the knitted wool cloth, while perpendicular to the plane of the knitted wool cloth the mechanical properties were those characteristic of the hydrogel itself. Similar phenomena, as described in example 1 were observed in both of these samples when the samples lost water. When these reinforced and laminate samples were exposed to tensile or shear forces, they failed exclusively through cohesive mechanism indicating that the interfacial strength between wool cloth and the polyvinyl alcohol hydrogel matrix is at least as high as the strength of the polyvinyl alcohol hydrogel matrix itself.

Example 3

A similar procedure was used as in example 1 except that the polyvinyl alcohol had a low degree of polymerization, having a viscosity of about 4 cps for a 4 weight % solution at 20° C., and a degree of hydrolysis of about 98% was dissolved in a 70/30 dimethylsulfoxide/ethanol solution with the concentration of the hydrogel being about 30 weight %. In this case, knitted acrylic fiber cloth was used for the reinforcement. The mechanical properties of the polyvinyl alcohol matrix were further improved by using heat treatment procedures by holding the sample in a vacuum at 90° C. for two hours.

The modulus, tensile strength and tear resistance of these samples in the plane of the knitted acrylic fiber cloth were those characteristic of the acrylic fiber cloth reinforcing material while perpendicular to the plane of the knitted wool cloth the mechanical properties were those characteristic of the hydrogel itself. Similar phenomena were observed again with the samples when they lost water, as in the Examples above. When these reinforced and laminated samples were exposed to tensile or shear forces, they failed exclusively through cohesive mechanism indicating that the interfacial strength between knitted acrylic fiber cloth and polyvinyl alcohol hydrogel matrix is at least as high as the strength of the polyvinyl alcohol hydrogel matrix itself.

Example 4

Using the procedure of example 1, a polyvinyl alcohol having a medium high degree of polymerization, having a viscosity of about 50 cps for a 4 weight % aqueous solution at 20° C., and a degree of hydrolysis of about 88%, was dissolved in a 80/20 dimethylsulfoxide/ethanol solution with a hydrogel concentration of about 30 weight %. A cloth of carbon fibers provided the reinforcement. The hydrogel of this example was not completely stable when submersed into water at room temperature for an extended period of time. The resulting a material with composite properties was very soft and delicate to the touch. The stability of the hydrogel was significantly improved by a heat treatment at 180° C. in a vacuum for 1 minute. After this heat treatment, the sample typically showed a weight loss of about 25 to 30 weight % in water at room temperature, but after losing that weight, the hydrogel samples became stable in the water for an extended period of time and showed nor further loss of weight. The modulus, tensile strength and tear resistance of these reinforced hydrogels in the plane of the carbon fiber cloth was that characteristic of the carbon fiber cloth while, perpendicular to the plane of the carbon fiber cloth, the mechanical properties were those characteristic of the hydrogel itself. Similar phenomena were observed again with both of these samples when the samples lost water as described in Example 1. When these reinforced and laminated samples were exposed to tensile or shear forces, they failed exclusively through cohesive mechanisms indicating that the interfacial strength between the carbon fiber cloth and the polyvinyl alcohol hydrogel matrix is at least as high as the strength of the polyvinyl alcohol hydrogel matrix itself.

Example 5

Similar procedures as was used in example 2 were used herein except that extrusion was used to create 7 mm diameter rods having imbedded in them continuous Vectra® fibers along their length. The polyvinyl alcohol hydrogel rods were extruded so that the fiber or fibers in each rod were positioned in different fashions. Sample (a) contained a single fiber in the middle of the rod. Sample (b) contained a single fiber along the outer surface in a straight fashion. Sample (c) had fiber wound as a spiral around the outside surface of the rod and sample (d) contained multiple fibers parallel to the axis of the rod. After physical cross linking and extraction of the solvent, as described in example 1, these samples underwent unique changes in the shape after a small loss of water and after the extraction of the solvent. Sample (a) was randomly warped, sample (b) was randomly twisted, while sample (c) had regular twisting, that is, a spiraling shape. Sample (d) behaved similarly as (a) except it was less warped and had a higher tensile strength since it contained more of the fibers in its cross section. All of these samples, as expected, in the direction of the fibers had modulus, tensile strength and tear resistance characteristic of the fibers. However, these rods were soft and delicate to the touch in a direction perpendicular to the axis of the rods, exhibiting properties typical for high water content polyvinyl alcohol hydrogels. When these reinforced and laminated samples were exposed to tensile or shear forces, they failed exclusively through cohesive mechanisms indicating that the interfacial strength between the fibers and the polyvinyl alcohol hydrogel matrix is at least as high as the strength of the polyvinyl alcohol hydrogel matrix itself.

Example 6

Similar procedures were used herein as described in Example 1 except that the polyvinyl alcohol concentration in the solution was 11 weight % and instead of using neat solution as in example 1, polyvinyl alcohol solution was first loaded with coarse sugar as a pore forming material wherein the sugar had an average particle size of about 0.8 mm. In this case, woven cloth made from natural silk was used for reinforcement. After the physical cross linking, and after water extraction of the sugar, the resulting material was soft, delicate and opaque. However, as expected, modulus, tensile strength and tear resistance of the samples were characteristic of the natural silk cloth, while perpendicular to the plane of the natural silk cloth, the mechanical properties were those characteristic of the hydrogel itself. Similar phenomena with shape as observed in Example 1 was observed with both of the samples as the samples were losing water, but less pronounced. When these reinforced and laminated samples were exposed to tensile or shear forces, they failed exclusively through cohesive mechanisms indicating that the interfacial strength between natural silk cloth and the polyvinyl alcohol hydrogel matrix is at least as high as the strength of the polyvinyl alcohol hydrogel matrix itself.

Example 7

Similar procedures were used as in Example 6 except that the hydrogel samples were reinforced with polyvinyl alcohol fiber cloth and were heat treated at 120° C. for 90 minutes. After the heat treatment the hydrogel matrix had collapsed cell walls, having exceptional tensile strength and tear resistance and compressibility and being somewhat abrasive to the touch. The hydrogel samples have modulus, tensile strength and tear resistance in the plane equivalent to those expected for polyvinyl alcohol fiber cloth, while perpendicular to the plane of the polyvinyl alcohol fiber cloth, the mechanical properties were those characteristic of the hydrogel itself. The change of shape upon partial water loss or gain was less pronounced in these samples after they were subjected to heat treatment as compared to those without the heat treatment. When these reinforced and laminate samples were exposed to tensile or shear forces, they failed exclusively through cohesive mechanism indicating that the interfacial strength between the polyvinyl alcohol fiber cloth and the polyvinyl alcohol hydrogel matrix is at least as high as the strength of the poly vinyl alcohol hydrogel matrix itself.

Example 8

Similar procedures were used as in example 6 except that the hydrogel samples were molded into rods having natural silk filaments imbedded in the middle of the rod. After they had been physically cross linked at low temperature and all solvents had been removed, the rod was heat treated at 120° C. for 90 minutes. After the heat treatment, the pore forming material was removed and the result was a rod having collapsed cell walls. The rods had good tensile strength and tear resistance, and had exceptional compressibility and were somewhat abrasive to the touch. The silk filament reinforced hydrogel rods had modulus, tensile strength and tear resistance equivalent to those expected of silk filaments. However, these rods were exceptionally soft and delicate to the touch in a direction perpendicular to the long axis of the rods. When these reinforced and laminated samples were exposed to tensile or shear forces, they failed exclusively through cohesive mechanisms indicating that the interfacial strength between natural silk filaments and the polyvinyl alcohol hydrogel matrix is at least as high as the strength of the polyvinyl alcohol hydrogel matrix itself.

Example 9

Similar procedures were used as in Examples 6 and 7 except that the polyvinyl alcohol concentration in solution was 1 weight % and polyvinyl alcohol fiber cloth were used for reinforcement. After heat treatment at 120° C. for 90 minutes, very fluffy reinforced polyvinyl alcohol sponges were obtained. The sponges were very soft, and had reasonably good strength and had good tear resistance, were somewhat abrasive and had exceptional compressibility. The mechanical properties of the materials with composite properties in the plane of the polyvinyl alcohol fiber cloth were equivalent to those of the polyvinyl fiber cloth itself. The catastrophic failure of the sample takes place through the cohesive failure mechanism as indicated in earlier examples.

Example 10

Similar procedures were used as in Example 1, 4, and 6 except that the following colorants were added to the polyvinyl alcohol solution in separate molds: methylene blue, Bonney's blue and various food colorants. Another separate sample was also made containing homogeneously dispersed barium sulfate as a radio opaque material. The observations of physical properties were essentially the same as described in the corresponding examples except that the samples were colored.

Example 11

Similar procedures were used as in Example 6 except the following: before granular sugar was loaded into the polyvinyl alcohol solution, in one sample, short natural silk fibers and in the second sample, short polyvinyl alcohol fibers, having average lengths of 5 mm, were added to the solutions at ten weight % as compared to the hydrogel weight fraction. Silk and polyvinyl alcohol fibers were homogeneously dispersed throughout the hydrogel sample. The rest of the sample preparation procedures were the same as described in Example 6. After physical cross linking and after extraction of the sugar with water, the short fiber reinforced cellular polyvinyl alcohol hydrogel was relatively soft, having improved tensile strength and tear resistance as compared to cellular polyvinyl alcohol hydrogel matrices not reinforced with the fibers as expected for short fiber reinforced hydrogel matrices. The catastrophic failure of the sample takes place through the cohesive failure mechanism as indicated by the samples supra.

Example 12

Polyvinyl alcohol having a high degree of polymerization and having a viscosity of about 66 cps for a 4% aqueous solution at 20° C., and a high degree of hydrolysis of 99.3%, was dissolved in dimethylsulfoxide solution with a polyvinyl alcohol concentration of about 10 weight %. Dissolution was carried out at 120° C., under nitrogen atmosphere, while continuously stirring for 2 hours. Then, 20 grams of distilled water was poured into 400 ml beakers together with 0.74 grams of sodium laurel sulfate and 0.90 grams of DC-194 surfactant (Dow Corning Corporation, Midland, Mich.), while nitrogen bubbled through the solution. The aqueous solution was vigorously mixed at room temperature for 5 minutes using a high speed stirrer equipped with blender blades. This produced a froth having about 15 times higher volume as compared to the initial water volume. Then, 20 grams of the polyvinyl alcohol solution in dimethylsulfoxide was added slowly while maintaining the high speed mixing with the final polyvinyl alcohol concentration in the froth being about 5 weight %. The froth was slowly cooled to about 15° C. that resulted in a stable froth that was then poured into molds. In one case, the mold contained jute cloth placed on the entire bottom surface of the rectangular mold with the depth of the mold being 4 mm. Then, polyvinyl alcohol froth, still kept at about 15° C., was poured onto the cloth to completely fill the mold. In the case of a second rectangular mold, polyvinyl froth was poured into the mold to fill only the half of its depth and then linen cloth was placed on the top of that polyvinyl forth layer. Additional polyvinyl alcohol froth was added to the mold to fill the rest of the mold. In both cases, the molds containing the cloth were placed into a freezer at a temperature of −18° C. and kept at that temperature for 8 hours. Molds were then taken out of the freezer and the cellular polyvinyl alcohol hydrogels were allowed to thaw. The cellular hydrogels were very soft, delicate and had low tensile strengths and low tear strengths. However, modulus, tensile strength and tear resistance of the over-all a material with composite properties in the direction of the plane of the sample were those of the corresponding cloths. The catastrophic failure of the sample takes place through the cohesive failure mechanism as indicated in the examples, supra. The cellular polyvinyl alcohol hydrogel was unstable in water and collapsed to a large extent when placed in a water bath.

Example 13

Similar procedures were used as in Example 12, except that after the a material with composite properties had been physically cross linked at low temperature, it was immediately place into acetone to extract the dimethylsulfoxide and water. Extraction was carried out by holding the samples in an acetone bath for 8 hours and then fresh acetone was used to replenish every 8 hours during the next 24 hours of extraction time. At the end of the 24 hours, the samples were taken out of the acetone and placed in a hood overnight to completely remove acetone. While the reinforced cellular polyvinyl alcohol structure was still holding acetone it was quite strong and firm. After the acetone was completely removed, the cellular structure became a semi-solid, porous structure. Finally, after this solvent treatment, the dry cellular structure was fully re-hydrated with water and it became appreciably stronger and more stable in water than the original sample of Example 12. The catastrophic failure of the sample takes place through the cohesive failure mechanism as indicated in earlier examples.

Example 14

Similar procedures as was used in Example 13 were used herein except that once all of the acetone was removed from the materials with composite properties; it was placed into a vacuum oven and evacuated for 30 minutes. Then it was heat treated to 130° C. for 120 minutes and allowed to cool to room temperature while still under vacuum. Heat-treated samples were placed into a water bath to re-hydrate, which resulted in a very fine, soft, open celled hydrogel sponge supported with cloth. This cellular hydrogel had very thin cell walls, that is, collapsed cell walls. The hydrogel itself is strong, tough and has reasonable tear resistance and has exceptional dimensional stability. The modulus, tensile strength and tear resistance of the overall a material with composite properties in the plane of the cloth was that of the corresponding cloth. The catastrophic failure of the sample takes place through the cohesive failure mechanism as indicated in the examples, supra.

Example 15

Similar procedures were followed as in Examples 12, 13, and 14, except that polyvinyl alcohol fibers having an average length of about 1.5 mm were added to the solution and then the solution was frothed. Polyvinyl alcohol fibers were added at a 15 weight % level as compared to the weight of the polyvinyl alcohol and no cloth was used for additional reinforcement. The cellular structure was solvent and heat-treated. The hydrogel had significantly increased tensile strength and tear resistance as compared to corresponding hydrogels without the addition of fibers.

Example 16

Similar procedures were followed as in examples 12, 13 and 14, except that frothed polyvinyl alcohol was extruded into shapes of 5 mm diameter rods having continuous polyvinyl alcohol filaments imbedded parallel to the long axis of the rod. Physical properties in a transversal direction were those of corresponding cellular polyvinyl alcohol hydrogels. However, modulus, tensile strength and tear resistance in the direction of the continuous polyvinyl alcohol filaments was that characteristic of the polyvinyl alcohol filaments. The catastrophic failure of the sample takes place through the cohesive failure mechanism as indicated in the examples, supra.

Example 17

Similar procedures as used in Examples 2 was used herein except that the polyvinyl alcohol solution was cast onto an assembly analogous to Band Aid® strips. Polyvinyl alcohol solution was poured onto the cotton gauze surface of the strips to create a hydrogel having a thickness of about 1 mm. The hydrogel was complexed with iodine by submersing the hydrogel into a solution of iodine. This article can be used in wound and burn healing applications providing the ability to dispense disinfectant in a controlled manner, provide protection for the injured skin, provide a non-adhering surface, and maintain moisture in a healing tissue.

Example 18

The same procedure was used herein as was used in Example 17 except that the polyvinyl alcohol solution had a concentration of two weight %. A small amount of polyvinyl alcohol solution was poured onto an assembly analogous to the Band Aid strips of Example 17 and the excess polyvinyl alcohol solution was allowed to run off creating a coated or impregnated cotton gauze structure. The volume of the solution that was poured onto the cotton gauze surface of the strip was sufficient to completely coat the surface of the cotton fibers and create a thin hydrogel coating only on the fiber network without creating a continuous hydrogel surface or film supported by the structure. This approach allowed the complete surface modification of the cotton gauze and also allowed it to complex a sufficient amount of iodine by submersing the coated cotton gauze into a solution of iodine. This article can be used in wound and burn healing applications providing the ability to dispense disinfectant in a controlled manner, provide protection for the injured skin, maintain moisture, provide a non-adhering surface to a healing tissue and allow air accessibility when necessary.

Example 19

Similar procedures as was used in Example 6 were used herein except that the polyvinyl alcohol solution loaded with granular sugar was cast onto the assembly analogous to the Band Aid strips of Example 17. The polyvinyl alcohol solution was loaded with granular sugar and was placed onto the cotton gauze surface of the strip to create a cellular polyvinyl alcohol hydrogel on the surface of the cotton gauze having a height of about 2 mm. The hydrogel on the strip was obtained by cooling the assembly to about −15° C. for 8 hours. Then, after extraction of the sugar, the hydrogel was complexed with iodine in the usual manner. This article can be used in wound and burn healing as well.

Example 20

Similar procedures as was used in Example 2 were used herein except that the polyvinyl alcohol solution was poured onto the surface of hard polystyrene into which cellulose fibers had been previously imbedded. In this case, cellulose fibers were imbedded into a polystyrene surface in the following manner: first, the surface of the polystyrene was softened and partially dissolved with hydrocarbon solvents such as acetone, toluene and the like, and then, cellulose fibers were partially imbedded into the softened polystyrene surface, and finally the solvent was allowed to evaporate to lock a portion of the cellulose fibers into the polystyrene surface. This produces an article having a dual surface where one surface is hard polystyrene and the other surface is that of a chosen type and in the nature of a hard, soft and/or delicate polyvinyl alcohol hydrogel.

Example 21

Similar procedures as was used in Example 20 were used herein except that the polyvinyl alcohol solution was poured onto the surface of a poly(dimethyl siloxane) cured film into which polyvinyl alcohol fibers had been previously partially imbedded. In this case, polyvinyl alcohol fibers were partially imbedded into the surface of the siloxane film by first casting a curable poly(dimethyl siloxane) material, then partially imbedding into it the polyvinyl alcohol fibers and then curing the siloxane material. This produced an article having a dual surface wherein one surface is hydrophobic, liquid water impermeable, water vapor highly permeable and the other surface is that of a chosen type and in the nature of a hard, soft, and/or delicate, hydrophilic polyvinyl alcohol hydrogel.

Example 22

Similar procedures were used herein as in Example 21 except that cellular polyvinyl alcohol hydrogel was created on the surface of the poly(dimethyl siloxane) film. This was accomplished by first partially imbedding the polyvinyl alcohol fibers into a cured poly(dimethyl siloxane) film and then placing polyvinyl alcohol solution loaded with salt particles on the film. In the second case, cotton gauze was imbedded into the surface of the siloxane film. Cotton gauze was imbedded into the polydimethysiloxane film by first extruding curable siloxane film and then placing cotton gauze onto the surface of the uncured film, and finally allowing the film to cure. This produces an article having a dual surface wherein one surface is hydrophobic, liquid water impermeable, water vapor highly permeable and the other surface is that of a chosen type and in the nature of a hydrophilic hydrogel.

Example 23

Two polyvinyl alcohol solutions from the same polyvinyl alcohol polymer, having different concentrations, were prepared. One solution contained polyvinyl alcohol polymer having a high degree of polymerization and having a viscosity of about 66 cps for a 4% aqueous solution at 20° C., and a high degree of hydrolysis of 99.3%. It was dissolved in an 80/20 mixture of dimethylsulfoxide and water with a concentration of about 25 weight %. The second solution had a concentration of 5 weight percent. These two solutions were cast sequentially (a) into a mold to form a slab having a 2 mm thickness and (b) into a mold to form an 8 mm diameter rod having 50 mm long section of one solution and 50 mm long section of the second solution. In another sample, these solutions were co-extruded into rods and 4 mm thick sheets. In both cases, samples were then placed into a freezer at −18° C. for 8 hours and the solvent was extracted with water. The samples resulted in two sections with widely differing physical properties one having low tear strength, high water content and the other having high tear strength, low water content. The catastrophic failure of this sample takes place through the cohesive failure mechanism.

Example 24

The same solutions of polyvinyl alcohol as described in example 23 were used to make cubes consisting of complex structures obtained by combining two polyvinyl alcohol solutions simultaneously, resulting in a unitary cube having the two polyvinyl alcohol bulk hydrogels interlocking and intertwining throughout the body of the cube. The simultaneous combining of both solutions in a mold in a certain pattern was carried out using two syringes that are capable of being moved freely in a plane above the mold surface. Once the cube mold is completely filled with polyvinyl alcohol solutions, it was cooled at −18° C. for eight hours and washed with water to remove solvents. The resulting polyvinyl alcohol hydrogel cube has a complex response to tensile and compressive forces as the result of the complex composition. The catastrophic failure of this sample takes place through the cohesive failure mechanism.

Example 25

The same polyvinyl alcohol solutions that were used in example 23 were used except that the object having the complex structure consisting of the interlocking polyvinyl alcohol bulk hydrogels was built without the mold, that is, they were freely laid out on the platform in a mode similar to ink-jet dispensing. Two polyvinyl alcohol solutions were dispensed in this controlled manner creating a desired pattern using syringes that can move freely in the plain parallel to the surface of the platform. The platform is located and partially submersed in the bath that contains a gelling media such as a solution of a salt or non-solvent. As the object is being built, the platform submerges, causing the submerged portions of polyvinyl alcohol solutions to gel, creating continuously and simultaneously the unitary object having the desired intricate, complex, intertwining and interlocking composition consisting of the polyvinyl alcohol bulk hydrogels. The catastrophic failure of the sample takes place through the cohesive failure mechanism.

Example 26

Polyvinyl alcohol having a high degree of polymerization and having a viscosity of about 66 cps for a 4% aqueous solution at 20° C., and a high degree of hydrolysis of 99.3% was dissolved in an 80/20 mixture of dimethylsulfoxide and water with a concentration of about 10 weight %. This solution was poured into a rectangular mold measuring 20 mm×20 mm×10 mm and then it was loaded with salt particles and placed into a freezer to form a hydrogel. After the salt was extracted with water, the rectangular cellular polyvinyl alcohol hydrogel was obtained. This sample was then encapsulated with bulk hydrogel made from the same polyvinyl alcohol solution by pouring a small portion of the hydrogel solution into a larger rectangular having a measurement of 30 mm×30 mm×20 mm and the first rectangular cellular hydrogel that had been prepared was placed into the larger mold and additional polyvinyl alcohol solution that was prepared secondly was poured around and on the top to completely encapsulate the cellular hydrogel. It was then placed in a freezer to make the second hydrogel. This a material with composite properties structure has a soft interior because it contains sponge and significantly higher modulus at or near walls of the object originating from the continuous bulk polyvinyl alcohol hydrogel envelope, i.e. walls, of the a material with composite properties object. The catastrophic failure of this sample takes place only through the cohesive failure mechanism.

Example 27

Similar to the example 24, frothed polyvinyl alcohol solution was combined with bulk polyvinyl alcohol hydrogel resulting in a complex structure composed of intertwining cellular and bulk polyvinyl alcohol hydrogels in a co-continuous or semi-continuous fashion. The catastrophic failure of this sample took place through a cohesive failure mechanism.

Example 28

Similar to the example 24, frothed polyvinyl alcohol solution was combined with polyvinyl alcohol solution containing a pore forming material. After gelling the polyvinyl alcohol cellular matrices and extraction of the pore forming material, the resulting structures had a complex structure composed of two intertwining, different types of cellular polyvinyl alcohol hydrogels in a co-continuous or semi-continuous fashion. The catastrophic failure of this sample took place through a cohesive failure mechanism.

The examples that have been provided herein are some of the typical possibilities of the making of structures according to this invention. These examples are not intended to limit the scope of the invention.

What I claim is:
1. A composite structure comprising:
a first physically cross linked polyvinyl alcohol based matrix derived from a first physically crosslinkable polyvinyl alcohol hydrogel; and
a second physically cross linked polyvinyl alcohol based matrix derived from a second physically crosslinkable polyvinyl alcohol hydrogel,
wherein the first physically crosslinkable polyvinyl alcohol hydrogel differs from the second physically crosslinkable polyvinyl alcohol hydrogel by a concentration of the polyvinyl alcohol polymer in the first solution differing from a concentration of a polyvinyl alcohol polymer in the second solution.
2. A composite structure comprising:
a first physically cross linked polyvinyl alcohol based matrix derived from a first physically crosslinkable polyvinyl alcohol hydrogel; and
a second physically cross linked polyvinyl alcohol based matrix derived from a second physically crosslinkable polyvinyl alcohol hydrogel,
wherein the first physically crosslinkable polyvinyl alcohol hydrogel differs from the second physically crosslinkable polyvinyl alcohol hydrogel by a degree of hydrolysis of the polyvinyl alcohol polymer in the first solution from a degree of hydrolysis of a polyvinyl alcohol polymer in the second solution.

* * * * *